(12) United States Patent
Torre et al.

(10) Patent No.: US 9,851,264 B2
(45) Date of Patent: Dec. 26, 2017

(54) HIGH-PRESSURE COLORIMETRIC MEASUREMENT CELL

(71) Applicant: UNIVERSITE DE PAU ET DES PAYS DE L'ADOUR, Pau (FR)

(72) Inventors: Jean-Philippe Stephane Torre, Sainte Colombe (FR); Frederic Cedric Plantier, Pau (FR); Laurent Christian Noel Marlin, Barbazan-Debat (FR)

(73) Assignee: UNIVERSITE DE PAU ET DES PAYS DE L'ADOUR, Pau (FR)

( * ) Notice: Subject to any disclaimer, the term of this patent is extended or adjusted under 35 U.S.C. 154(b) by 386 days.

(21) Appl. No.: 14/417,313

(22) PCT Filed: Jul. 26, 2013

(86) PCT No.: PCT/EP2013/065820
§ 371 (c)(1),
(2) Date: Jan. 26, 2015

(87) PCT Pub. No.: WO2014/016414
PCT Pub. Date: Jan. 30, 2014

(65) Prior Publication Data
US 2015/0204735 A1     Jul. 23, 2015

(30) Foreign Application Priority Data
Jul. 27, 2012 (FR) .................... 12 57319

(51) Int. Cl.
*G01K 17/00*   (2006.01)
*G01N 25/48*   (2006.01)
*G01K 1/14*    (2006.01)

(52) U.S. Cl.
CPC .............. *G01K 17/00* (2013.01); *G01K 1/14* (2013.01); *G01N 25/4893* (2013.01); *G01N 25/4886* (2013.01)

(58) Field of Classification Search
None
See application file for complete search history.

(56) References Cited

U.S. PATENT DOCUMENTS

| 7,112,904 B2 * | 9/2006 | Akiyama ................ C30B 15/30 |
| | | 310/103 |
| 7,946,753 B2 * | 5/2011 | Kar ..................... B01F 7/00416 |
| | | 366/266 |

FOREIGN PATENT DOCUMENTS

GB         1003831 A  *  9/1965   ......... B01F 7/00008

OTHER PUBLICATIONS

Rocheleau (Hawaii Energy and Environmental Technologies (HEET) Initiative Phase Aug. 4, 2006 Final Technical Report, Sections 4.3-4.3.3 pp. 35-55).*
Backman et al ("A System of Microcalorimeters", Pure & Applied Chemistry vol. 66 No. 3 p. 375-382, 1994).*

(Continued)

*Primary Examiner* — Clayton E Laballe
*Assistant Examiner* — Leon W Rhodes, Jr.
(74) *Attorney, Agent, or Firm* — Young & Thompson

(57) ABSTRACT

The supporting device (10) includes: a body (14), designed to be mounted on an enclosure of a calorimeter, an end-fitting (34) for supporting the measurement cell (12), including elements (36) for fastening the measurement cell (12) on that supporting end-fitting (34), and fluid flow members in the measurement cell (12), able to control the pressure in that measurement cell (12).

16 Claims, 8 Drawing Sheets

(56) References Cited

OTHER PUBLICATIONS

Google search results for "Setaram hydrates "circulation cell"".*
Setaram Instrumentation: C80 Calvet Calorimeter, Mar. 2009, XP002696806, http://www.experta-benelux.com/brochures/C80.pdf.
International Search Report, dated Nov. 5, 2013, from corresponding PCT application.

* cited by examiner

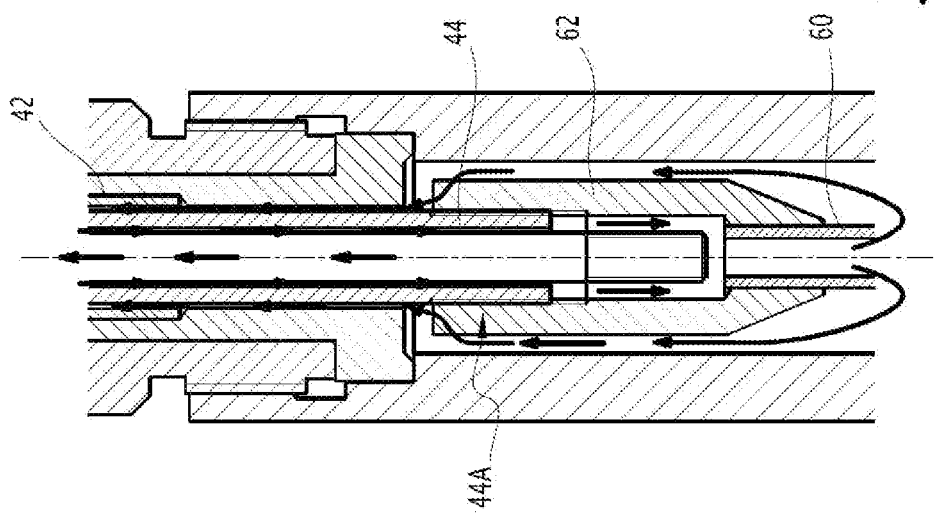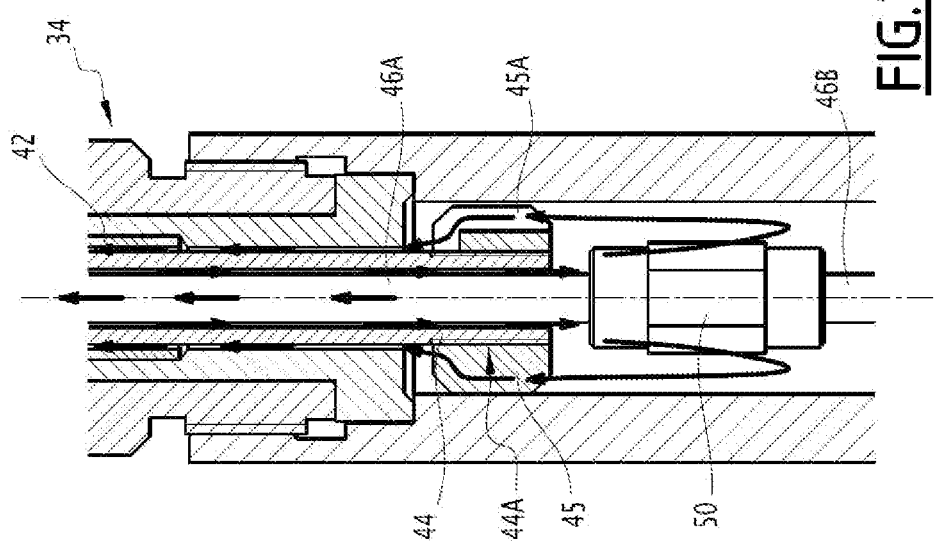

HIGH-PRESSURE COLORIMETRIC MEASUREMENT CELL

The present invention relates to an assembly of a calorimetric measurement cell and a support device for said measurement cell, as well as a calorimeter comprising such an assembly.

Calvet-type calorimeters are already known from the state of the art. Such a calorimeter in particular comprises a temperature-controlled enclosure (also called "calorimetric block"), in which a measurement cell is housed, designed to receive a study substance, as well as a reference cell, in order to allow a differential analysis of the heat flow exchanged between those two cells.

Traditionally, the measurement cell is surrounded by a first set of thermocouples, making it possible to measure a first heat flow between the study substance and the enclosure. Likewise, the reference cell is surrounded by a second set of thermocouples to measure a second heat flow between that cell, which may or may not contain a reference fluid, and the enclosure.

Such a calorimeter enables the experimental measurement of certain thermodynamic properties of the substance introduced into the measurement cell, such as state change enthalpies, phase transition temperatures or heat capacities.

In particular, one may wish to perform measurements for a study substance during a reaction, in particular a chemical, physical or physicochemical reaction.

For example, said study substance is a liquid in which soluble gas is injected. In that case, it is generally necessary to agitate the measurement cell in order to allow rapid solubilization of the gas in the liquid. Other chemical reactions likewise require agitation, in particular to homogenize the substance.

To that end, different cells are already known. The so-called "batch mixing cell" makes it possible, by breaking a small blister, to mix two substances introduced into the cell beforehand (one in the blister and the other at the bottom of the cell).

The simple "mixing circulation liquid cell" is made to mix two liquids, using a very small torque, that may enter and exit the cell, but does not exist with pressurized operation.

Another way of agitating the cells is to add a complicated device to the calorimeter that makes it possible to switch that calorimeter, and is very tedious to implement.

The present invention in particular aims to resolve these drawbacks, by providing a support device for a measurement cell of a calorimeter, allowing agitation of a substance in the measurement cell, even for pressurized measurements, while having an easy-to-implement structure.

To that end, the invention in particular relates to an assembly of a calorimetric measurement cell and a support device for a measurement cell, characterized in that the support device comprises:
- a body designed to be mounted on a temperature-controlled chamber of a calorimeter (or calorimetric block),
- an end-fitting for supporting the measurement cell, comprising means for fastening the measurement cell on that supporting end-fitting,
- fluid flow members in the measurement cell, able to control the pressure in that measurement cell.

Advantageously, the device according to the invention comprises means for agitating the measurement cell, for example an agitating rod that extends in particular inside the measurement cell. Such an agitating rod allows a sufficient agitation to perform mixing or agitation of single substances or mixtures of fluids in that measurement cell, without requiring switching the calorimeter. Furthermore, the device according to the invention makes it possible to perform a pressurized agitation, using fluid flow members. In fact, the fluid flow members make it possible to introduce fluid into the cell, or to remove fluid from the cell, which allows dynamic pressure control.

The fluid is for example pressurized upstream from the fluid flow members, by external means, for example by connecting the device to a bottle or reservoir for pressurized gas, or using a compressor.

Advantageously, the body of the assembly is hollow and has a circumferential side wall delimiting a first chamber and a second chamber in the hollow body that are separated by a tight sealing element, the fluid flow members comprising:
- a fluid intake member, emerging in the first chamber through the side wall, and a fluid discharge member, emerging in the second chamber through the side wall,
- an outer tubular member, extending from the second chamber to the supporting end-fitting, so as to emerge in the second chamber on the one hand, and in the measurement cell when it is fastened to the supporting end-fitting on the other hand, and
- an inner tubular member, extending coaxially to the inside of the outer tubular member, from the first chamber, through the sealing element, as far as the supporting end-fitting, so as to emerge in the first chamber on the one hand, and in the measurement cell when it is fastened to the supporting end-fitting on the other hand.

Thus, the device according to the invention makes it possible to gradually cause a first component to flow toward a second component previously introduced into the measurement cell, to perform progressive mixing, unlike a "mixing cell" of the state of the art in which the components to be mixed are introduced into the cell together before the measurement.

The structure of the supporting device according to the invention makes it possible to control the pressure in the measurement cell, using fluid introduction and discharge members, and inner and outer tubular members.

In particular, it is possible to introduce a fluid gradually through the fluid intake member, then to convey the fluid through a conduit delimited by the inner tubular member as far as the measurement cell.

Likewise, it is possible to discharge a fluid, by conveying fluid from the measurement cell, through a conduit delimited between the outer tubular member and the inner tubular member, as far as the fluid discharge member.

Thus, the fluid intake and discharge members make it possible to cause a fluid to flow continuously, with a controlled pressure or flow rate, in the measurement cell, in particular to inject a liquid or gaseous reagent therein, or to bleed the measurement cell.

These intake and discharge members also make it possible to maintain a given pressure level in the measurement cell, for example when a reaction, in particular a chemical, physical or physicochemical reaction, absorbing or generating gas, takes place in the measurement cell. For example, it is possible to provide chemical reactions consuming $CO_2$, or reactions during which clathrates or hydrates form and separate. In fact, in the latter case, gas is absorbed during the formation of the clathrates or hydrates, and gas is emitted during their separation.

Owing to the device according to the invention, it is possible to perform variable-temperature and constant-pressure measurements.

A supporting device according to the invention may further comprise one or more of the following features, considered alone or according to all technically possible combinations.

- The supporting device comprises a dip tube, arranged in the extension of the inner tubular member, designed to extend in the measurement cell when it is fastened to the supporting end-fitting.
- The supporting device comprises a stirrer, extending along a rod axis from the body to the supporting end-fitting, and in the measurement cell when it is fastened to the supporting end-fitting, the stirrer being rotatable around that rod axis.
- The stirrer extends coaxially to the inside of the inner tubular member, from the first chamber to the supporting end-fitting, and in the measurement cell when it is fastened to the supporting end-fitting.
- The stirrer comprises at least one agitation element, arranged on the stirring rod beyond the supporting end-fitting so as to be positioned inside the measurement cell when it is fastened to that supporting end-fitting.
- The agitation element is formed by at least one generally annular washer, having an inner contour rotatably connected to the stirrer, and an outer contour provided with fins.
- Each washer is secured to the stirrer so as to have a washer axis forming a non-zero angle with the rod axis.
- The assembly comprises at least two washers, the washer axes of which are parallel, and/or at least two washers positioned symmetrically relative to a plane perpendicular to the rod axis.
- The agitation element is formed by a worm screw, or a mobile stirring device of the propeller, turbine or anchor type.
- The stirrer comprises a first part, extending from the first chamber to the supporting end-fitting, and a second part extending beyond the supporting end-fitting so as to be positioned inside the measurement cell when it is fastened to that supporting end-fitting, the second part being secured in rotation with the first part, and each washer being supported by the second part.
- The assembly comprises a motor comprising an output shaft, and a coupling member arranged on the body, comprising an intermediate shaft designed to be coupled to the output shaft on the one hand, and coupled to the stirrer on the other hand.
- The assembly comprises a motor comprising an output shaft, and magnetic means for coupling the output shaft to the stirrer.
- The supporting end-fitting being designed to be fastened to a generally cylindrical cell, the means for fastening the cylindrical cell on the supporting end-fitting comprising a threaded part arranged on the supporting end-fitting, complementary with a tapped part of the cylindrical cell.

The invention also relates to a calorimeter of the type comprising an enclosure, characterized in that it comprises:

- an assembly of a measurement cell and a supporting device for the measurement cell as previously defined, housed in the enclosure,
- a first set of thermocouples surrounding the measurement cell,
- a reference cell, housed in the enclosure, and
- a second set of thermocouples surrounding the reference cell.

The invention also relates to the use of a calorimeter having the above features to study the formation and separation of gas hydrates or clathrates.

The invention will be better understood upon reading the following description, provided solely as an example and done in reference to the appended figures, in which:

FIG. 7 is a partial view of the lower part shown in FIG. 2, showing the flow of fluid in the measurement cell;

FIG. 9 is a view similar to FIG. 7, showing the flow of fluid in the lower part of the measurement cell shown in FIG. 8;

Figure 1:
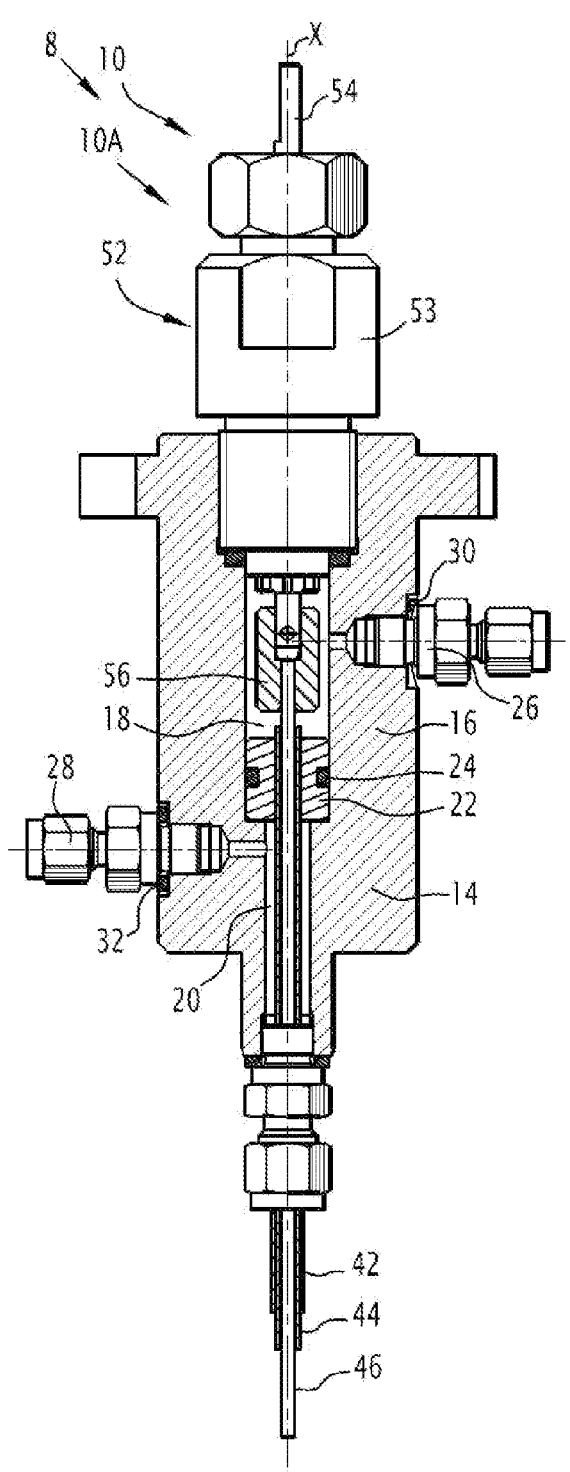
FIG. 1 is a sectional view of an upper part of a supporting device according to one example embodiment of the invention.

The figures show an assembly 8 of a measurement cell 12 and a supporting device 10 for the measurement cell 12, designed to equip a calorimeter, in particular a Calvet-type calorimeter. An upper part 10A of the supporting device 10 is shown in FIG. 1, and a lower part 10B of the supporting device 10 is shown in FIG. 2.

It will be recalled that the Calvet-type calorimeter comprises a temperature-controlled enclosure, in which the measurement cell 12 and a reference cell are housed. A first set of thermocouples surrounds the measurement cell 12, to measure a first heat flow between the inside and the outside of the measurement cell 12, and a second set of thermocouples surrounds the reference cell to measure a second heat flow between the inside and the outside of said reference cell.

The measurement cell 12 is designed to receive a study substance for which one wishes to perform a thermal analysis, and the reference cell is generally empty or filled with a product whose thermal characteristics are perfectly known, in order to allow a differential analysis of the heat flows by comparing the measurement cell and the reference cell.

Figure 2:
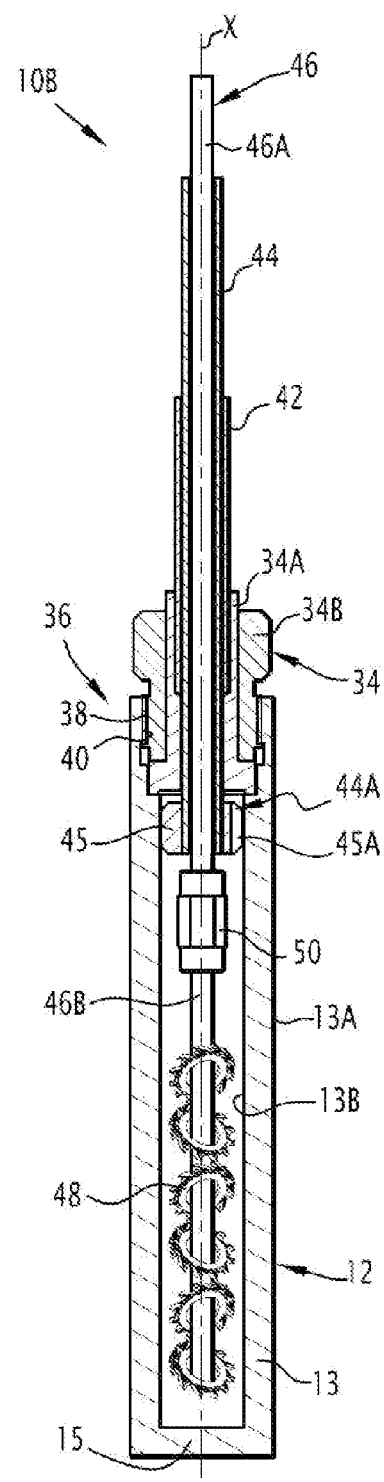
FIG. 2 is a sectional view of the lower part of the supporting device of FIG. 1, in particular comprising a supporting end-fitting for a measurement cell.

Typically, and as in the case of the present description, the measurement cell 12, shown in more detail in FIG. 2, has a generally hollow cylindrical shape, delimited by a cylindrical wall 13 having an outer surface 13A and an inner surface 13B, and by a bottom wall 15 closing the cell 12 at the lower end. The measurement cell 12 is, however, open at its upper end, in order to allow a substance to be thermally analyzed to be inserted into that measurement cell 12.

FIG. 1 shows the upper part 10A of the supporting device 10. This upper part 10A comprises a hollow body 14 designed to be mounted on the thermostatic enclosure (not shown) of the calorimeter. In particular, this hollow body 14 forms a "wellhead", designed to be positioned at the apex of a well arranged in the temperature-controlled enclosure of the calorimeter, closing that well. For example, the well has a diameter of 17 mm and a depth of 550 mm.

According to the described embodiment, the hollow body 14 has a general shape of revolution around an axis X, and therefore has a cylindrical circumferential side wall 16. The supporting device 10 comprises fluid flow members in the measurement cell 12, in particular making it possible to increase the pressure in that measurement cell 12 beyond the atmospheric pressure. The fluid introduced into the device may be pressurized using external means, for example a gas can or a pressurized reservoir, or using a compressor.

To that end, the circumferential side wall 16 delimits a first chamber 18 and a second chamber 20 in the hollow body 14 that are separated from each other by a tight sealing element 22, in particular comprising a sealing gasket 24.

The fluid flow members comprise a fluid intake member 26, emerging in the first chamber 18 through the side wall 16, and a fluid discharge number 28, emerging in the second chamber 20 through the side wall 16.

Advantageously, in order to ensure good sealing of the first 18 and second 20 chambers, sealing means 30 are arranged between the intake member 26 and the side wall 16, and sealing means 32 are arranged between the discharge member 28 and the side wall 16. Said sealing members 30, 32 for example each comprise an annular sealing gasket pinched between a circumferential shoulder of the intake member 26, the discharge member 28, respectively, and a circumferential shoulder arranged on the side wall 16.

The intake member 26 as well as the discharge number 28 can be connected to a respective external conduit (not shown), able to convey a fluid from a feed device to that intake member 26, from the discharge device 28 to a receiving device, respectively. Furthermore, each of the intake 26 and discharge 28 members comprises a respective valve in order to allow or prohibit the passage of a fluid through that intake 26 or discharge 28 member.

As shown in FIG. 2, the supporting device 10 comprises a supporting end-fitting 34 in its lower part 10B to support the measurement cell 12.

The supporting end-fitting 34 comprises means 36 for fastening the measurement cell 12 on said supporting end-fitting 34. In particular, the fastening means 36 comprise a threaded part 38 arranged on the supporting end-fitting 34, complimentary with a tapped part 40 of the cell 12. The tapped part 40 is arranged at the upper end of the cell 12, on the inner surface 12B.

For example, the supporting end-fitting 34 comprises a stationary element 34A, with a general shape of revolution around the axis X, and a moving element 34B, coaxial to the stationary element 34A, and movable around the stationary element 34A and the axis X. In that case, the threaded part 38 is arranged on the moving element 34B. Thus, the moving element 34B forms a nut, which may be screwed into the measurement cell 12 by rotating around the stationary element 34A.

The fluid flow members further comprise an outer tubular member 42 and an inner tubular member 44 that are coaxial, in particular connecting the upper part 10A of the supporting device 10 to the lower part 10B.

The outer tubular member 42 extends from the second chamber 20 to the supporting end-fitting 34, so as to emerge on the one hand in the second chamber 20, and on the other hand in the measurement cell 12 when the latter is fastened to the supporting end-fitting 34.

Furthermore, the inner tubular member 44 extends coaxially to the outer tubular member 42, from the first chamber 18, through the sealing element 22, up to the supporting end-fitting 34. Thus, the inner tubular member 44 emerges on the one hand in the first chamber 18 and on the other hand in the measurement cell 12 when the latter is fastened to the supporting end-fitting 34.

Advantageously, the inner tubular member 44 has a threaded distal end 44A, on which a tapped centering member 45 is screwed. Said centering member 45 is designed to cooperate with an inner wall of the cell 12 to allow good centering of the tubular members 42, 44 relative to that cell 12. It will be noted that said centering member 45 has at least one passage 45A for the fluid, in order to allow the fluid passage from the cell 12 to the outer tubular member 42.

A fluid introduced into the first chamber 18, through the intake member 26, is next conveyed in a first conduit delimited by the inner tubular member 44 up to the inside of the measurement cell 12, in which it can mix with a component, for example a liquid, previously introduced into that measurement cell 12.

Likewise, when a fluid must be discharged from the measurement cell 12, for example to regulate the pressure in that measurement cell 12, or when a chemical reaction in the cell 12 causes the formation of a gas to be discharged, that fluid is conveyed through a second conduit defined between the inner tubular member 44 and the outer tubular member 42 as far as the chamber 20, in order to be discharged through the discharge member 28.

The fluid flow members therefore allow dynamic control of the pressure in the cell 12, by controlling the supply and discharge of fluid, for example gas, in that cell 12.

The fluid flow members are partially shown in FIG. 7. The fluid enters through the intake member 26, flows in said first conduit up to the measurement cell 12, fills the measurement cell 12 (which may further contain another fluid, in particular a liquid), then flows in said second conduit, to leave via the discharge member 28.

The fluid flow members make it possible to produce a pressurized fluid flow. That fluid flow in particular aims to regulate the pressure inside the cell 12. In particular, when the pressure decreases in the cell 12, fluid is admitted by the inlet, and when the pressure increases in the cell, fluid is removed by the outlet.

The fluid flow also makes it possible to perform gas sweeping of the cell particularly simply. To that end, gas is admitted via the inlet, flows in the measurement cell 12, and leaves via the outlet. That operation, for regulating or bleed purposes, may be done with or without agitation, under pressure.

In addition to possible pressure regulation, the fluid flow members allow pressurization in the cell 12. To that end, the intake member 26 is connected to an external pressurizing device, for example a pressurized gas can or a compressor.

It will be noted that the assembly 8 is configured to operate under pressure. The assembly 8 is in particular sealed when the access to the intake 26 and discharge 28 members is closed (for example using valves connected to those intake and discharge members), such that the assembly 8 is able to maintain pressure when the cell 12 contains pressurized gas.

As previously indicated, it is possible to regulate that pressure, by keeping it at a predefined value in the cell, and it is possible to perform gas sweeps while operating under pressure.

In some cases, it is necessary to agitate the sample contained in the cell 12, for example to allow rapid solubilization of a gas in a liquid and to prevent a dissolved gas concentration gradient from forming between the surface of the liquid and the bottom of the cell 12. Agitation also makes it possible, for measurements done with polyphasic mediums such as emulsions or suspensions, to maintain the homogeneity of the analyzed medium. The agitation may also be necessary to conduct a pressurized chemical reaction in the measurement cell 12, in order to homogenize the reactive mediums. Lastly, for a compound crystallization reaction formed under pressure by combining liquid and gas (such as clathrates and gas hydrates), agitation allows continuous renewal of the contact surface between the liquid and gas (mixing the solid), in order to avoid the formation, at the gas/liquid interface, of a solid crust impermeable to gas that would block the conversion of the liquid, and thus in order to maintain solubilization of the gas in the residual liquid.

In order to perform such agitation simply and effectively, the support device 10 comprises a stirrer 46, extending along a rod axis, here combined with the axis X, and extending coaxially to the inside of the inner tubular member 44, from the first chamber 18 to the supporting end-fitting 34, and in the measurement cell 12 when the latter is fastened to the supporting end-fitting 34. That stirrer 46 is rotatable around the axis X.

The stirrer comprises at least one agitation element 48 arranged on the stirrer 46 beyond the supporting end-fitting 34, so as to be positioned inside the measurement cell 12 when the latter is fastened to the supporting end-fitting 34.

In the illustrated example, the stirrer 46 comprises at least one generally annular washer 48, having an inner contour rotatably connected to the stirrer 46, and an outer contour provided with fins allowing mixing of the substance contained in the cell 12 when the stirrer 46 is rotated. Such a washer 48 is generally called "tooth lock washer". In the illustrated example, the stirrer 46 bears six washers 48.

Each washer 48 is secured to the stirrer 46 so as to have a washer axis forming a non-zero angle with the rod axis X. In other words, these washers 48 are welded in staggered rows on the stirrer 46.

In the illustrated example, the washers 48 are distributed in two groups of washers, such that within each group, the axes of the washers 48 of that group are parallel to each other. Furthermore, each washer of each group is placed symmetrically with respect to a washer of the other group relative to a plane perpendicular to the rod axis X. This arrangement of the washers 48 allows optimized agitation of the substance in the measurement cell 12.

Alternatively, the stirrer 46 may bear any other type of agitation element, for example a worm screw or mobile agitation members of the propeller, turbine, anchor or other type.

Advantageously, for easy mounting of the stirrer 46, the latter comprises a first part 46A, extending from the first chamber 18 to the supporting end-fitting 34, and a second part 46B extending beyond the supporting end-fitting 34 so as to be positioned inside the measurement cell 12 when it is fastened to the supporting end-fitting 34. The second part 46B is secured in rotation with the first part 46A, using a coupling element 50 of the traditional type. In that case, the washers 48 are supported by the second part 46B. Thus, the second part 46B can be disassembled, so as to be used only when agitation is necessary.

In order to rotate the stirrer 46 around the axis X, the supporting device 10 comprises a motor (not shown) comprising an output shaft connected in rotation with the stirrer 46. To that end, the supporting device 10 comprises a coupling member 52 arranged on the hollow body 14, so as to close the first chamber 18 sealably. That coupling member 52 in particular comprises a body 53, with a shape complementary to a housing arranged in the body 14, as well as an intermediate shaft 54, designed to be coupled with the output shaft of the motor, and extending through the body 53 of the coupling member 52 as far as the inside of the chamber 18. The intermediate shaft is coupled to the stirrer 46 in the first chamber 18, using a coupling element 56 of the traditional type.

Figure 14:
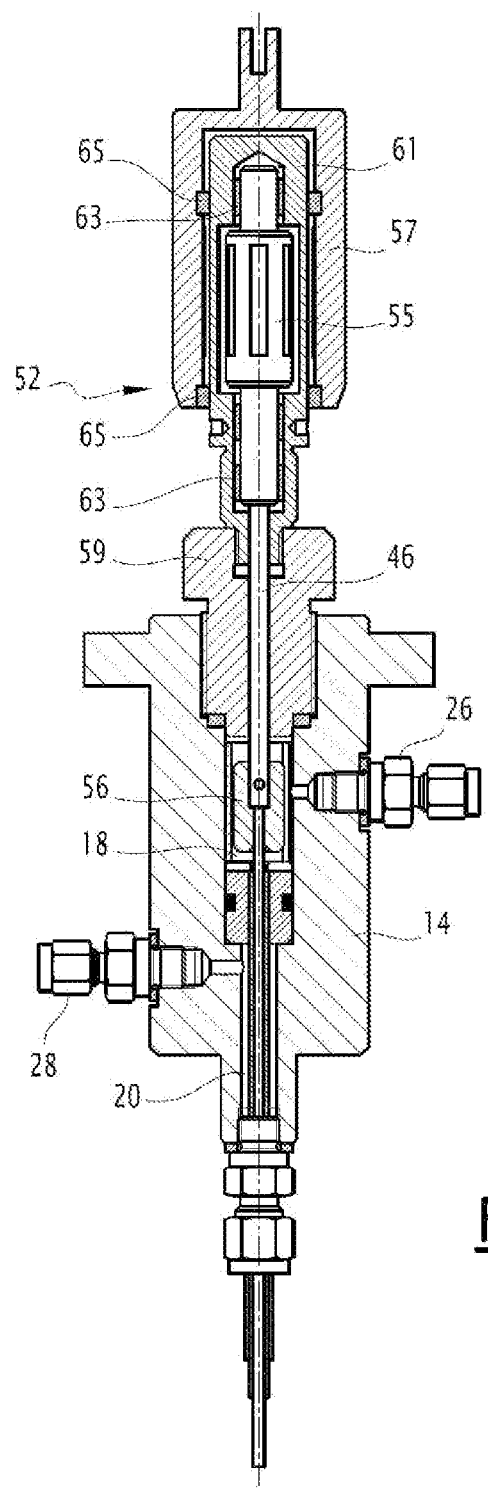
FIG. 14 is a view similar to FIG. 1 of an upper part of a supporting device according to one alternative embodiment of the invention.

Alternatively, the stirrer 46 can be coupled to the motor shaft by magnetic means instead of the mechanical means described above, as shown in FIG. 14. In that case, the stirrer 46 is for example provided with a first magnetic element 55, in particular an electromagnet, and the motor shaft is provided with a second magnetic element, in particular a permanent magnet 57. Such magnetic coupling means have the advantage of not requiring the passage of a coupling member through the walls of the hollow body 14, and therefore do not require additional sealing means.

More particularly, in this alternative, the coupling member 52 comprises a connecting end-fitting 59, with a shape complementary to a housing formed in the body 14, and sealably connected to that body 14. The coupling member 52 also comprises a housing 61, sealably fastened on the connecting end-fitting 59. Said housing 61 comprises an inner area in which the first magnetic element 55 is housed. Advantageously, first rotational guiding means 63, for example ball bearings or rolling bearings or main bearings, are arranged between the first magnetic element 55 and the housing 61.

Furthermore, the second magnetic element 57 is arranged around the housing 61. Advantageously, second rotational guiding means 65, for example ball bearings or rolling bearings or main bearings, are arranged between the second magnetic element 57 and the housing 61.

When the second magnetic element 57 is rotated by the output shaft of the motor, it rotates the first magnetic element 55 by magnetic field effect. Since that first magnetic element 55 is connected to the stirrer 46, the latter is also rotated around its axis.

This alternative primarily makes it possible to secure the cell 12 while avoiding any risk of gas leak at the driving system of the stirrer 46, such a leak being able to pose safety risks, in particular when the gas is flammable. In fact, in the case of the mechanical coupling previously described, a gas leak risk may exist between the coupling member 52 and the body 14, in particular when the coupling member 52 is provided with a sealing gasket that wears out over time.

Thus, when the stirrer 46 is driven by magnetic coupling, it is no longer necessary to arrange a sealing member between the rotating part formed by the stirrer 46 and the stationary part. In that case, it is possible to put the cell 12 at a higher operating pressures than in the case of mechanical coupling, while increasing the safety level.

It will be noted that any other magnetic means for rotational driving of the stirrer 46 can be considered.

It clearly appears that the supporting device 10 according to the invention makes it possible to work under pressure, under agitated conditions, with a significant specimen volume and while ensuring dynamic pressure control, all while being adapted to the geometric constraints related to the use of a Calvet-type calorimeter. In particular, it will be noted that the described supporting device 10 does not cause stress on the bulk of the measurement cell 12, such that it is possible to use a measurement cell having a relatively significant volume.

A device according to the invention, for example as described above, may for example be used to determine phase equilibrium conditions of a system simultaneously requiring (i) pressure resistance, (ii) agitation, and (iii) dynamic pressure control of the cell.

Thus, as an example, below we will describe the use of a device according to the invention to study the formation and separation of $CO_2$ hydrates and mixed hydrates containing both $CO_2$ and tetrahydrofuran ($CO_2$+THF). This family of compounds (hydrates and clathrates) is in particular described in more detail in the publication by Sloan, E. G., 2003. "Fundamental principles and applications of natural gas hydrates" Nature 426, 20, 353-359.

The aim is to determine the separation temperatures of these two hydrates at a constant pressure (yielding a point P-T on the equilibrium curve). For this experiment, a very low concentration of anionic surface active agent, sodium dodecyl sulfate (SDS) was added to the solution. SDS (under the concentration conditions used here) is a kinetic additive not modifying the equilibrium conditions (see in particular the publication by Torré, J.-P., Dicharry, C., Ricaurte, M., Broseta, D., Diaz, J., Renaud, X., 2011b. "$CO_2$ enclathration in a semi-continuous quiescent hydrate-forming reactor operated with pure $CO_2$ and water soluble additives", Proceedings of the 7th International Conference on Gas Hydrates (ICGH 2011), Edinburgh, 2011).

To that end, it is necessary to:
solubilize the $CO_2$ in the solution (contained in the cell) under pressure and agitation;
form both types of hydrates by cooling the system to a given temperature, under agitation and while keeping the pressure at a constant value (necessary gas supply);
separate the two hydrates formed by increasing the temperature at a given heating ramp, under agitation, while keeping the pressure constant (salting out gases).

Subsequently, the calorimetric response obtained during the heating phase has been analyzed to obtain the two separation temperatures of the formed hydrates. Lastly, the external results obtained are compared to other results published in the literature.

More particularly, the conditions of the experiment are defined below.

The gas used is $CO_2$.

The study substance is an aqueous solution containing 4 wt % of THF and 0.3 wt % of SDS. The mass of study substance introduced is 6.88 g.

The pressure in the cell is brought to 30.2±0.3 bars.

Lastly, the rotational speed of the agitator is 150 RPM.

The temperature-controlled enclosure is activated to perform a cooling phase, from an initial temperature of 20° C. to a final temperature of 1° C., with a heating ramp at an uncontrolled speed close to 0.1° C./min. The measurement cell is next kept at 1° C. for several hours, generally overnight.

The temperature-controlled enclosure is next activated to carry out a heating phase, from an initial temperature of 1° C. to a final temperature of 25° C., with a heat ramp at a controlled speed equal to 0.1° C./min.

The obtained results have been shown in FIGS. 3 to 6.

Figure 3:
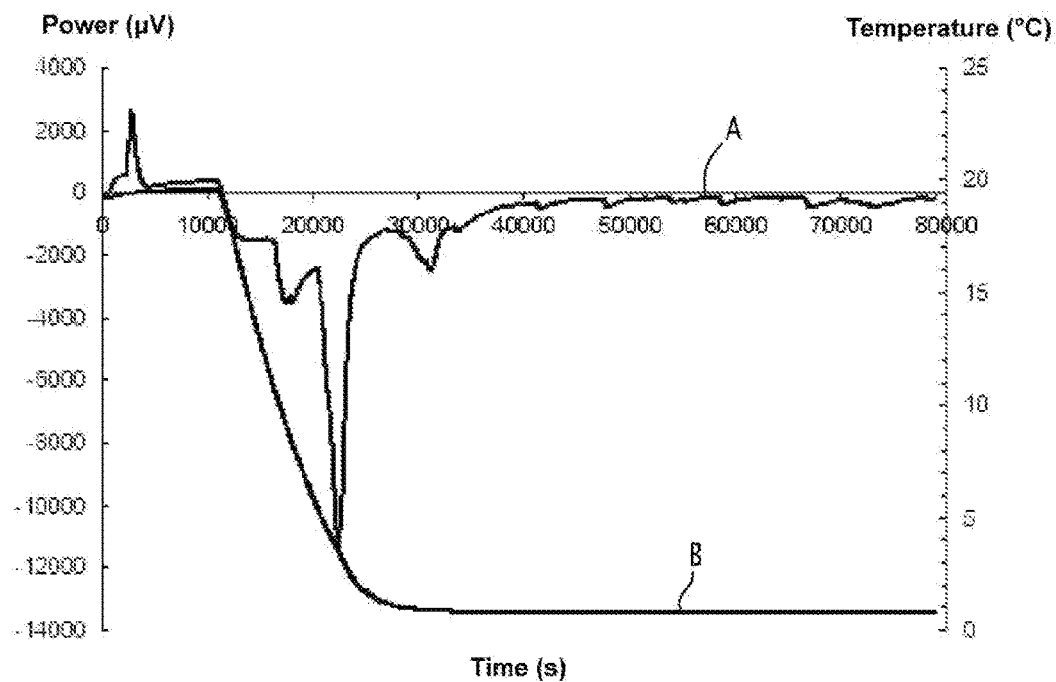
FIG. 3 is a thermograph obtained during a cooling phase of a method for studying a substance using a calorimeter according to the invention.

In particular, the thermograph obtained during the cooling phase, at a pressure P=30.2 bars, is shown in FIG. 3. In that FIG. 3, the evolution of the power is shown by curve A, and the evolution of the temperature by curve B.

It appears that the measured signal is not noised by the agitation. Furthermore, several peaks are obtained during cooling, but it is difficult to draw conclusions from them because of the meta-stability of the studied systems.

Figure 4:
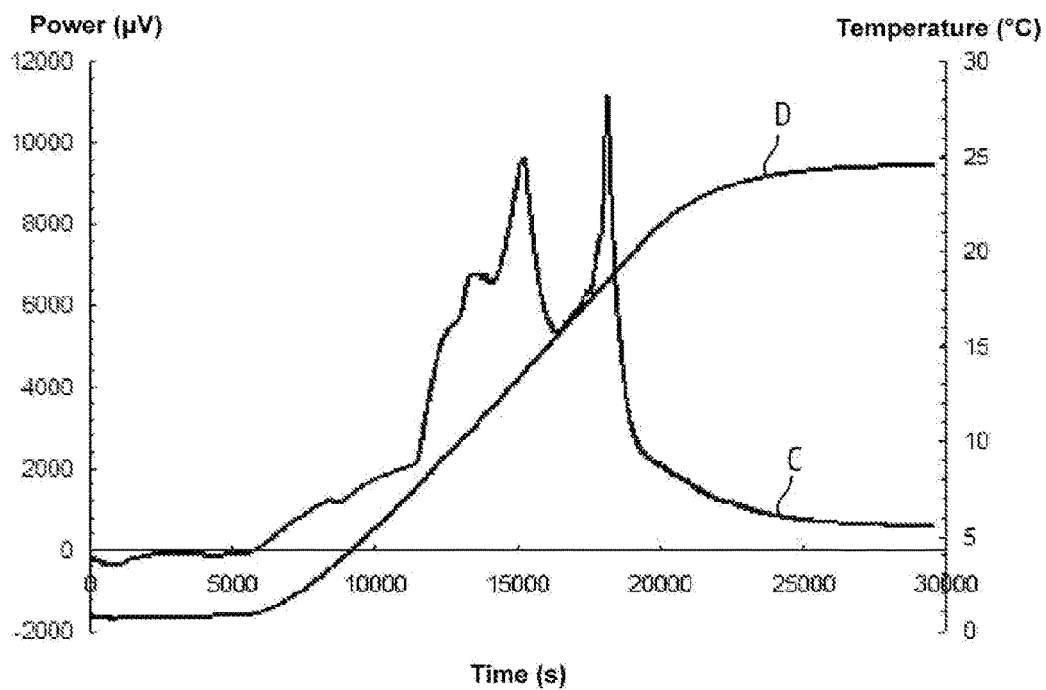
FIG. 4 is a thermograph obtained during a heating phase of the method for studying said substance using the calorimeter according to the invention.

The thermograph obtained during the heating phase, at a pressure P=30.2 bars, is shown in FIG. 4. In that FIG. 4, the evolution of the power is shown by the curve C, and the evolution of the temperature by the curve D.

It appears that the measured signal is not noised by the agitation. Furthermore, several peaks are obtained during the heating phase, those peaks corresponding to the various phase transitions.

Figure 5:
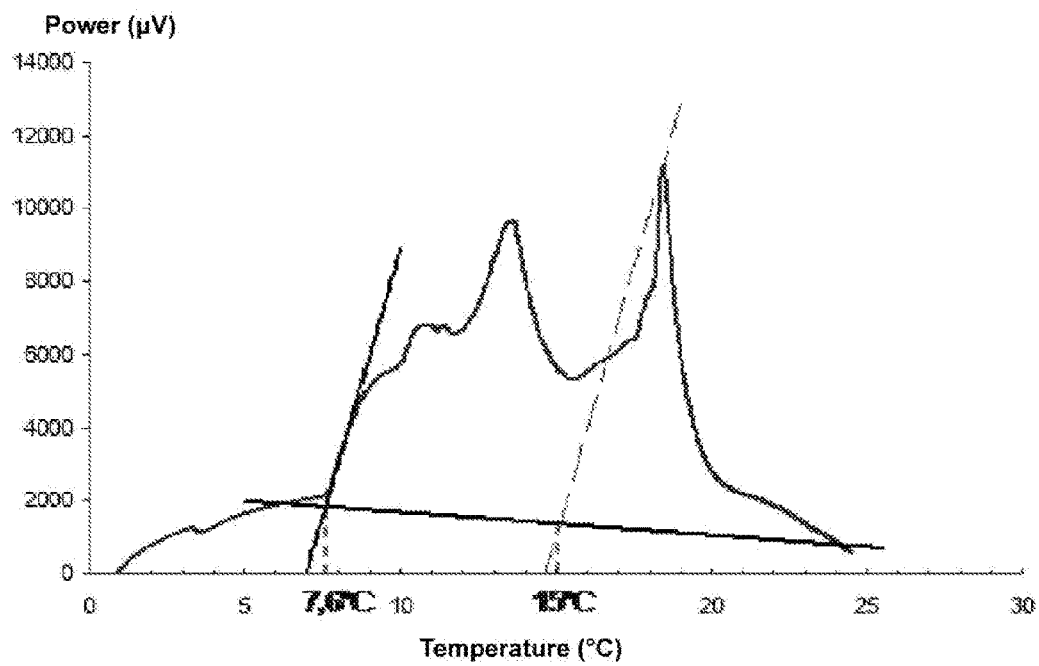
FIG. 5 is an operating graph of the thermograph of FIG. 4 for obtaining separation temperatures.

The exploitation method for the thermograph, known in itself, is shown in FIG. 5. The intersection of the tangent at the inflection point (given by the derived curve) of the first peak with the baseline is called the "onset point", and provides the separation temperature of the $CO_2$ hydrate at the experimental pressure (30.2 bars).

The last peak is attributed to the separation of the mixed hydrate (THS+$CO_2$) obtained for 4 wt % of THF. The separation temperature of the hydrate is then obtained by a projection on the baseline in a direction parallel to the linear rising edge of the first peak.

According to this FIG. 5, the obtained results are as follows. For a pressure of 30.2 bars (3.02 MPA), the separation temperature of the $CO_2$ hydrate is 7.6° C. (280.7 K), and the separation temperature of the THF+$CO_2$ mixed hydrate (4 wt % of THF) is 15° C. (288.1 K).

Figure 6:
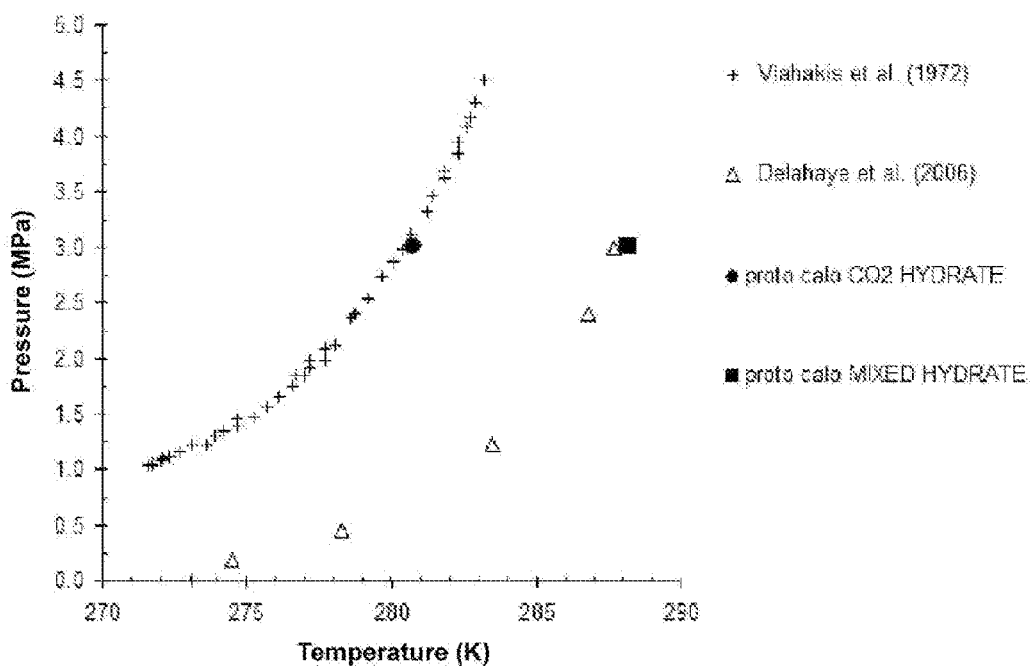
FIG. 6 is a comparison graph between experimental data obtained using the calorimeter according to the invention and data from the literature.

These results can be compared with the data accessible in the literature, as shown by FIG. 6, in particular with data from Vlahakis et al. (1972) for the equilibrium curve of the pure $CO_2$ hydrate, and data from Delahayte et al. (2006) for the equilibrium curve for the $CO_2$+THF mixed hydrate (4 wt % of THF).

Good agreement has been observed between the experimental data obtained with the device according to the invention and the data already published in the literature, demonstrating the performance of the described invention.

Other results obtained with the device according to the invention will be described below.

It should be noted that, to be able to measure the phase transition temperatures and energy phenomena precisely, it is necessary to perform temperature and enthalpy calibration of the cell 12. Such a calibration can be done traditionally, without any particular difficulties.

As an example, Table 1 below shows melting temperatures for pure bodies, obtained experimentally with the device according to the invention, and compared with those found in the literature (NIST).

In this table, $T_{fusion}\_ref$ corresponds to the reference temperatures found in the literature, and $T_{fusion}\_exp$ corresponds to the temperatures obtained experimentally.

TABLE 1

| Reference fluids (NIST) | $T_{fusion\_ref}$ (° C.) | $T_{fusion\_exp}$ (° C.) |
| --- | --- | --- |
| water | 0.00 ± 0.05 | 0.1 ± 0.1 |
| cyclohexane | 6.5 ± 0.3 | 6.7 ± 0.2 |
| n-$C_{12}$ | −9.7 ± 0.3 | −9.9 ± 0.2 |
| n-$C_{14}$ | 5.6 ± 0.9 | 5.3 ± 0.2 |
| n-$C_{16}$ | 18 ± 1 | 18.1 ± 0.2 |

It appears that the experimental results are in agreement with the values of the literature, with a precision estimated at ±0.2° C.

Figure 10:
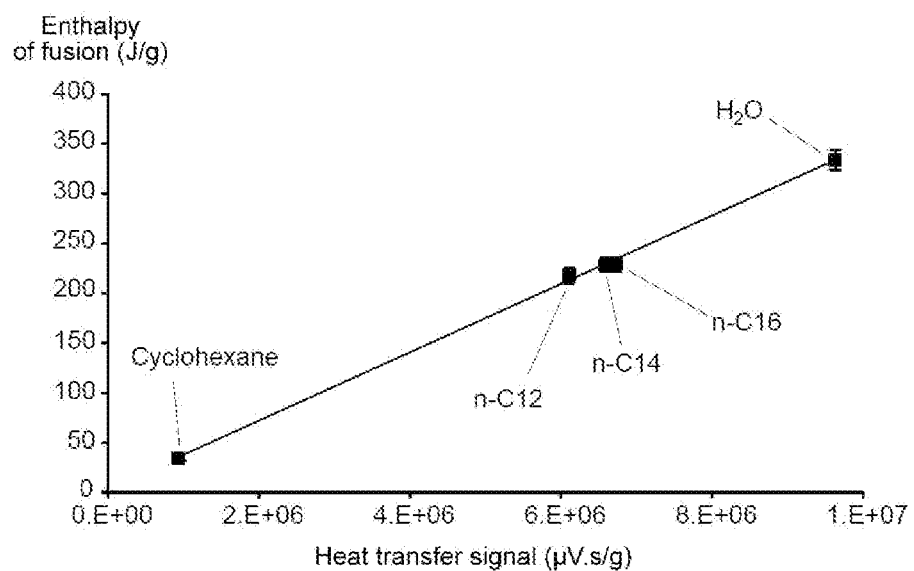
FIG. 10 is a graph showing a correspondence curve between an obtained calorimetric signal (on the X axis) and a value of the fusion enthalpies of pure bodies.

Furthermore, FIG. 10 shows a correspondence curve between the obtained calorimetric signal (on the X axis) and the value of the melting enthalpies of the pure bodies listed in Table 1 (on the Y axis). This correspondence curve makes it possible to determine the enthalpy calibration constant of the prototype, which is necessary to rise to thermodynamic and thermophysical data.

It appears that the calibration curve is a straight line passing through zero, extended over a wide range of energy levels (from 30 to 300 J/g). It is therefore simple to calibrate the device according to the invention using this method.

The beneficial effect of the agitation will be studied below.

Figure 11:
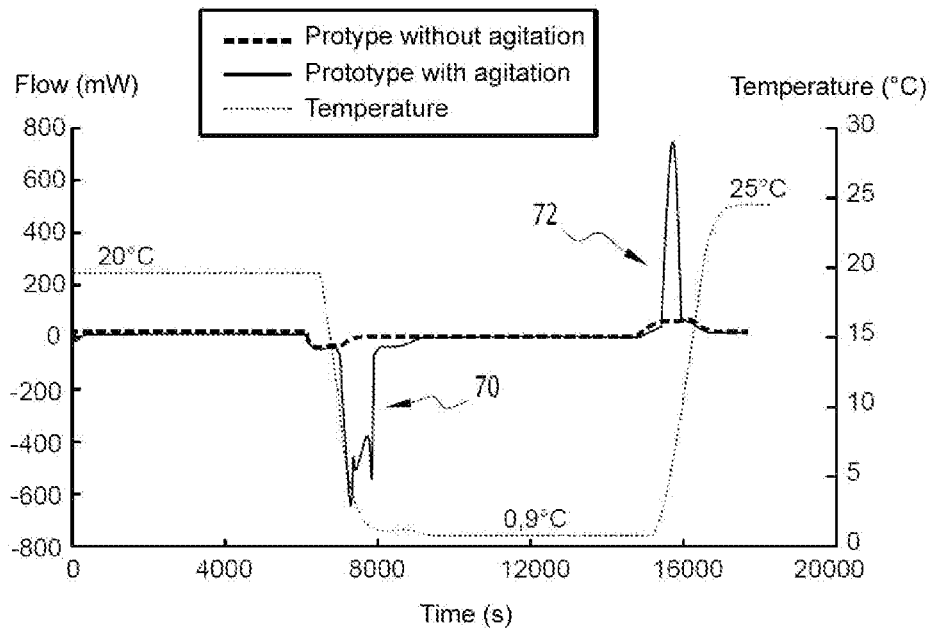
FIG. 11 is a graph obtained during a method for the thermodynamic study of a gas hydrate using a device according to the invention.

This beneficial effect is in particular illustrated by FIG. 11, in a practical gas hydrate thermodynamic case study, and more particularly $CO_2$ hydrates.

A known mass of water (for example, approximately 5 g) is introduced into the measurement cell 12 beforehand. Said measurement cell 12 is closed and installed at the bottom of the calorimetric well.

The air contained in the supporting device 10 is next discharged by $CO_2$ sweeping, using the fluid flow members.

The device 10 is next pressurized by $CO_2$, for example at 30.5 bars, using a $CO_2$ canister and an expander. The agitation is next activated, for example at a speed of 150 RPM (rotations per minute).

The device 10 is then left for several hours at 20° C. (regulated temperature) and under a constant pressure to perform solubilization of the $CO_2$ in the water.

It will be noted, as previously indicated, that the agitation of the cell 12 does not cause additional measurement noise compared to the case "without agitation" (in which exactly the same protocol is followed, but without activating the agitator).

The temperature of the cell 12 is next decreased to 0.9° C. to try to form the $CO_2$ hydrate. The pressure is kept constant in the device during cooling by the fluid flow members, allowing dynamic pressure control.

In the case where the cell 12 is agitated, FIG. 11 clearly shows an exothermic peak 70 during cooling, corresponding to the crystallization of the $CO_2$ hydrate in the measurement cell.

However, it appears that crystallization does not occur when the cell 12 is not agitated, even leaving the system at equilibrium (static) 0.9° C. for several hours.

In a final step, the temperature is increased to 25° C. with a precise heating speed ramp (for example, 0.1° C./min in the case at hand). When the cell 12 contains hydrates (case of agitation), an endothermic peak 72 is noted during heating, corresponding to the separation of the hydrate (the $CO_2$ is released from the solid).

However, no particular event is noted in the non-agitated case, since no hydrate has been formed.

The pressure is kept constant during the heating phase with the fluid flow members, allowing dynamic pressure control. The analysis of the peak 72 obtained upon the temperature increase makes it possible to determine the separation temperature of the hydrate (called "onset temperature") and calculate the enthalpy associated with that phenomenon (corresponding to the area below the peak).

Figure 12:
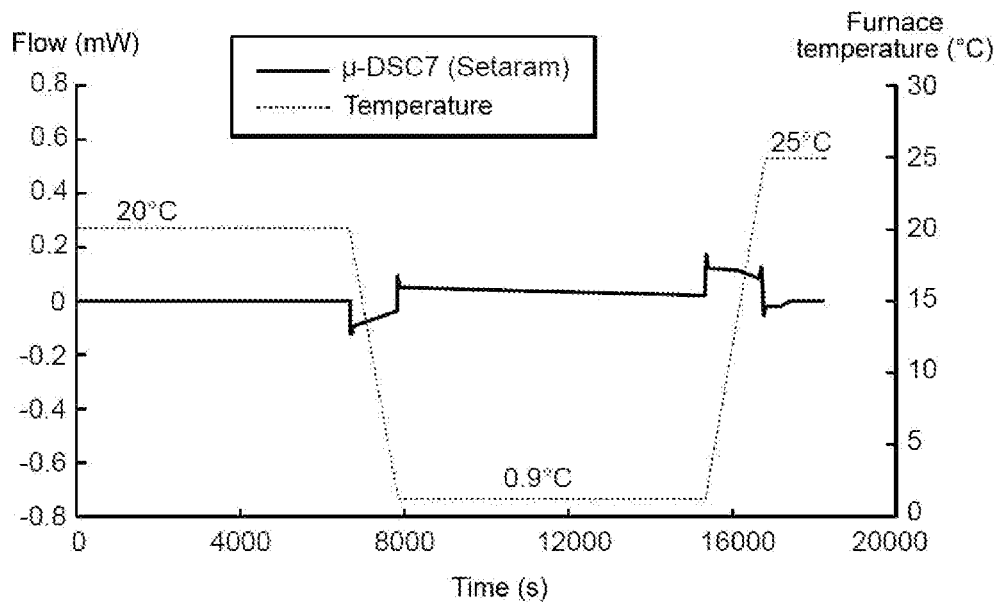
FIG. 12 is a graph similar to FIG. 11, obtained during a method for the thermodynamic study of a gas hydrate using a device known from the state of the art.

FIG. 12 shows the results obtained for a similar experiment (exactly the same ramp and temperature plateaus), but done on a traditional device, for example the micro-DSC7 from SETARAM, considered to be standard in terms of pressurized micro-calorimeters for studying gas hydrates. This FIG. 12 clearly shows that under these conditions, no crystallization is obtained, the cell not being agitated and having a smaller volume. In particular, no exothermic or endothermic peak is observed in this FIG. 12.

Thus, it clearly appears that the device according to the invention, making it possible to agitate the cell 12 under pressurized conditions, makes it possible to produce the crystallization, which clearly indicates the beneficial effect of the agitation to produce that crystallization under those conditions.

It will be noted that these results are reproducible. For example, Table 2 below shows the results obtained in terms of separation temperature ($T_{disso}$) and separation enthalpy ($\Delta H_{disso}$) for three tests done under the same conditions as those previously described to obtain the results of FIG. 11. It shows very good reproducibility of the obtained results.

TABLE 2

| | $T_{disso}$ (° C.) | $\Delta H_{disso}$ (J/$g_{eau}$) |
| --- | --- | --- |
| Test 1 | 7.5 ± 0.2 | 480 ± 10 |
| Test 2 | 7.6 ± 0.2 | 480 ± 10 |
| Test 3 | 7.7 ± 0.2 | 460 ± 10 |

Figure 13:
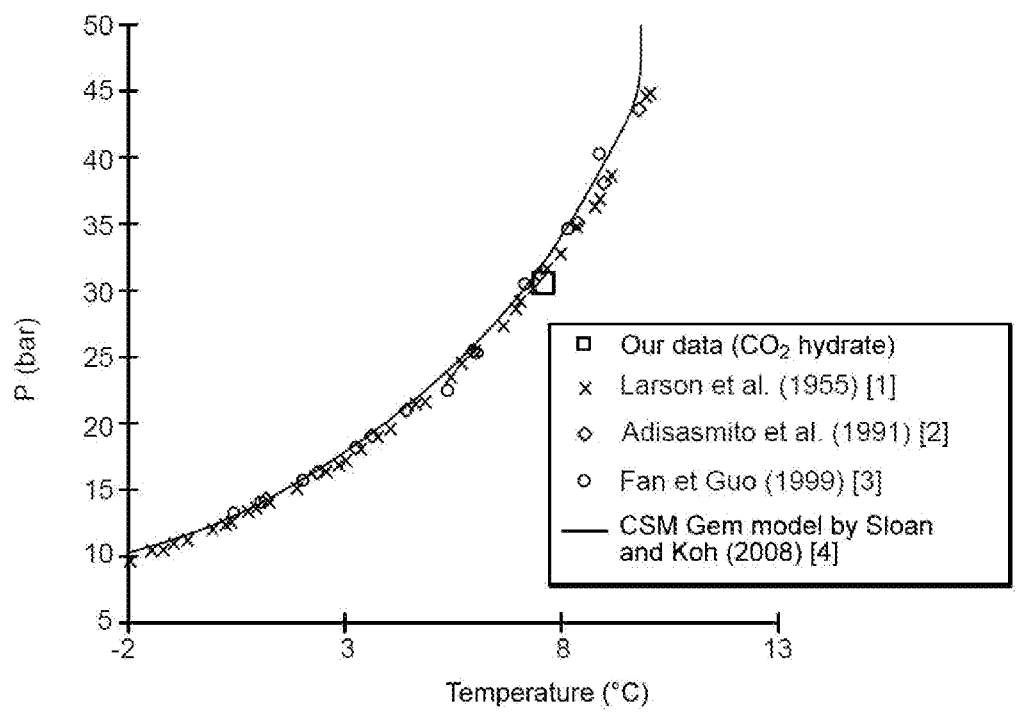
FIG. 13 is a graph comparing experimental results obtained using the device according to the invention with data from the literature.

FIG. 13 illustrates the comparison between the experimental results obtained for the separation temperature of the $CO_2$ hydrate at 30.5 bars of $CO_2$ (average of the results listed in Table 2) with the results from the literature, in particular the following publications:

[1] Larson, D., 1955. PhD Thesis, University of Illinois, Urbana, Ill., USA.

[2] Adisasmito S. et al. (1991). J. Chem. Eng. Data 36(1), 68-71

[3] Fan S. and Guo T.-M. (1999). J. Am. Chem. Soc. 44, 829-832

[4] Sloan, E. D and Koh, C. A., 2008. Clathrate hydrates of natural gases. 3rd edition. CRC Press, New York.

It is clearly shown that the experimental results obtained are in complete agreement with the data from the literature.

It will be noted that the invention is not limited to the embodiment previously described, but may assume various alternatives without going beyond the scope of the claims.

Figure 8:
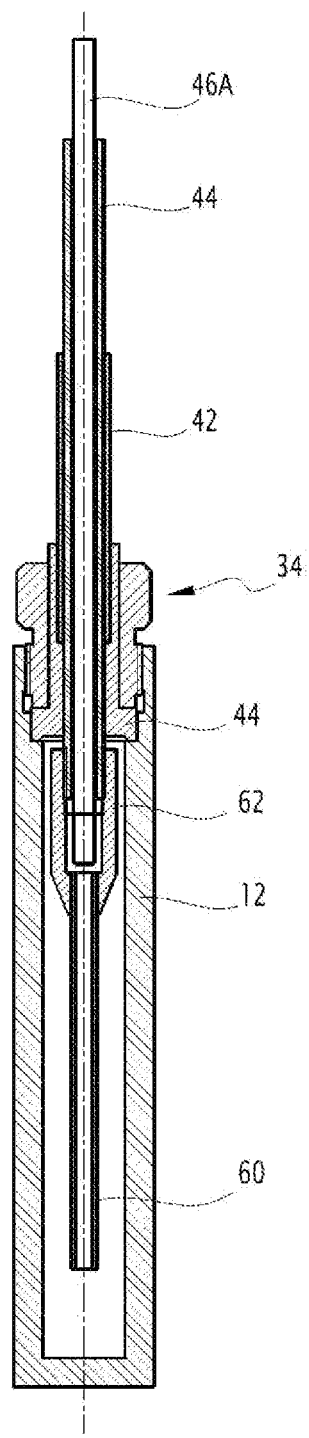
FIG. 8 is a view similar to FIG. 2 of a lower part of the supporting device according to an alternative embodiment.

In particular, the supporting device 10 may not comprise a stirrer. Thus, according to one alternative, shown in FIGS. 8 and 9, the supporting device 10 comprises a dip tube 60 in place of a stirrer 46.

This alternative is particularly advantageous in cases where it is necessary to bubble a pressurized gas in a liquid.

It will be noted that this alternative may be carried out using the same supporting device 10 as that previously described, in which the second part 46B of the stirrer is replaced by said dip tube 60.

To that end, the coupling element 50 is unscrewed. A connecting element 62, provided with the dip tube 60, at least partially tapped, is then screwed on the threaded end of the inner tubular member 44. The dip tube 60 is thus arranged in the extension of the inner tubular member 44, such that the fluid flowing in the first conduit passes through that dip tube 60 to reach the cell 12. Said dip tube 60 extends in the cell 12 enough to be submerged in a liquid previously introduced into the measurement cell 12, thus allowing bubbling in that liquid.

More particularly, the fluid flow members then work as follows, as partially shown in FIG. 9. The fluid, in particular gas, is introduced by the intake member 26, travels in the first conduit defined by the inner tubular member 44, then through the dip tube 60, to a level close to the bottom of the measurement cell 12, the liquid level initially being higher than the end of the dip tube. The gas then bubbles in the liquid contained in the cell 12, then leaves the device by traveling through the second conduit defined by the outer tubular member 42, to leave via the discharge member 28.

The invention claimed is:

1. An assembly of a calorimetric measurement cell and a support device for a measurement cell, wherein the support device comprises:
   a body, designed to be mounted on an enclosure of a calorimeter,
   a supporting end-fitting for supporting the measurement cell, comprising a fastener for fastening the measurement cell on that supporting end-fitting,
   fluid flow members in the measurement cell, able to control the pressure in that measurement cell, and
   a stirrer, extending along a rod axis from the body to the supporting end-fitting, and in the measurement cell when the measurement cell is fastened to the supporting end-fitting, the stirrer being rotatable around that rod axis,
   wherein the assembly is configured for performing a pressurized agitation in the measurement cell.

2. The assembly according to claim 1, wherein the body is hollow and has a circumferential side wall delimiting a first chamber and a second chamber in the body that are separated by a tight sealing element, the fluid flow members comprising:
   a fluid intake member, emerging in the first chamber through the circumferential side wall, and a fluid discharge member, emerging in the second chamber through the circumferential side wall,
   an outer tubular member, extending from the second chamber to the supporting end-fitting, so as to emerge in the second chamber on the one hand, and in the measurement cell when it is fastened to the supporting end-fitting on the other hand, and
   an inner tubular member, extending coaxially to the inside of the outer tubular member, from the first chamber, through the tight sealing element, as far as the supporting end-fitting, so as to emerge in the first chamber on the one hand, and in the measurement cell when this measurement cell is fastened to the supporting end-fitting on the other hand.

3. The assembly according to claim 2, wherein the support device comprises a dip tube, arranged in the extension of the inner tubular member, designed to extend in the measurement cell when this measurement cell is fastened to the supporting end-fitting (34).

4. The assembly according to claim 2, wherein the stirrer extends coaxially to the inside of the inner tubular member, from the first chamber to the supporting end-fitting, and in the measurement cell when this measurement cell is fastened to the supporting end-fitting.

5. The assembly according to claim 1, wherein the stirrer comprises at least one agitation element arranged on the stirrer beyond the supporting end-fitting, so as to be positioned inside the measurement cell when this measurement cell is fastened to the supporting end-fitting.

6. The assembly according to claim 5, wherein the agitation element is formed by at least one generally annular washer, having an inner contour rotatably connected to the stirrer, and an outer contour provided with fins.

7. The assembly according to claim 6, wherein each washer is secured to the stirrer so as to have a washer axis forming a non-zero angle with the rod axis.

8. The assembly according to claim 6, comprising at least two washers, having washer axes that are parallel.

9. The assembly according to claim 6, comprising at least two washers positioned symmetrically relative to a plane perpendicular to the rod axis.

10. The assembly according to claim 5, wherein the agitation element is formed by a worm screw.

11. The assembly according to claim 5, wherein the agitation element is formed by a mobile agitation device chosen among a propeller, a turbine and an anchor.

12. The assembly according to claim 2, wherein:
   the stirrer comprises at least one agitation element arranged on the stirrer beyond the supporting end-fitting, so as to be positioned inside the measurement cell when the measurement cell is fastened to the supporting end-fitting, and
   the stirrer comprises a first part, extending from the first chamber to the supporting end-fitting, and a second part extending beyond the supporting end-fitting so as to be positioned inside the measurement cell when this measurement cell is fastened to that supporting end-fitting, the second part being secured in rotation with the first part, and each agitation element being supported by the second part.

13. The assembly according to claim 1, comprising a motor comprising an output shaft, and a coupling member arranged on the body, comprising an intermediate shaft designed to be coupled to the output shaft on the one hand, and coupled to the stirrer on the other hand.

14. The assembly according to claim 1, comprising a motor comprising an output shaft, and a magnetic coupler for coupling the output shaft to the stirrer.

15. The assembly according to claim 1, wherein, the supporting end-fitting being designed to be fastened to a generally cylindrical cell, the fastener for fastening the cylindrical cell on the supporting end-fitting comprises a threaded part arranged on the supporting end-fitting, complementary with a tapped part of the cylindrical cell.

16. A calorimeter, comprising:
   an enclosure,
   an assembly of a measurement cell and a support device for the measurement cell, housed in the enclosure, the support device comprising:
      a body, designed to be mounted on an enclosure of a calorimeter,
      an end-fitting for supporting the measurement cell, comprising a fastener for fastening the measurement cell on that supporting end-fitting,
      fluid flow members in the measurement cell, able to control the pressure in that measurement cell, and
      a stirrer, extending along a rod axis from the body to the supporting end-fitting, and in the measurement cell when the measurement cell is fastened to the supporting end-fitting, the stirrer being rotatable around that rod axis, wherein the assembly is configured for performing a pressurized agitation in the measurement cell,
a first set of thermocouples surrounding the measurement cell,
a reference cell, housed in the enclosure, and
a second set of thermocouples surrounding the reference cell.

* * * * *

UNITED STATES PATENT AND TRADEMARK OFFICE
CERTIFICATE OF CORRECTION

PATENT NO. : 9,851,264 B2  
APPLICATION NO. : 14/417313  
DATED : December 26, 2017  
INVENTOR(S) : Jean-Philippe Stephane Torre et al.

It is certified that error appears in the above-identified patent and that said Letters Patent is hereby corrected as shown below:

On the Title Page

Amend Item (54) to read as follows:
--(54) HIGH-PRESSURE CALORIMETRIC MEASUREMENT CELL--.

Signed and Sealed this
Twenty-ninth Day of May, 2018

Andrei Iancu
*Director of the United States Patent and Trademark Office*